US00PP28398P3

(12) United States Plant Patent
Laurens

(10) Patent No.: US PP28,398 P3
(45) Date of Patent: Sep. 19, 2017

(54) APPLE TREE NAMED 'INOLOV'

(50) Latin Name: ***Malus domestica* Borkh.**
Varietal Denomination: Inolov

(71) Applicant: Institut National de la Recherche Agronomique, Paris (FR)

(72) Inventor: François Laurens, Beaucouze (FR)

(73) Assignee: Institut National de la Recherche Agronomique, Paris (FR)

( * ) Notice: Subject to any disclaimer, the term of this patent is extended or adjusted under 35 U.S.C. 154(b) by 363 days.

(21) Appl. No.: 14/544,341

(22) Filed: Dec. 26, 2014

(65) Prior Publication Data

US 2016/0192554 P1 Jun. 30, 2016

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

(56) References Cited

PUBLICATIONS

GTITM UPOVROM Citation for 'Inolov' as per FR PBR 20316; Nov. 21, 2013; 1 page.*

* cited by examiner

*Primary Examiner* — Kent L Bell
(74) *Attorney, Agent, or Firm* — Michelle Bos Legal LLC

(57) ABSTRACT

'Inolov' is a new apple tree notable for its resistance to scab, late harvest maturity, and flavorful fruit.

6 Drawing Sheets

Latin name: *Malus domestica* Borkh.
Variety denomination: 'Inolov'.

BACKGROUND OF THE VARIETY

'Inolov' is a new and distinct cultivar of apple tree (*Malus domestica* Borkh). This new cultivar is the product of a controlled cross of 'X4712' Gala (not patented) by 'X6908' (not patented), carried out at Angers, France in 1992. 'Inolov' was initially selected for propagation and further experimentation because of its flavorful fruit and resistance to common strains of scab. 'Inolov' was first asexually reproduced by grafting at Angers, France in 1994, and has since been observed to remain true to type over successive asexually propagated generations.

BRIEF DESCRIPTION OF THE VARIETY

'Inolov' is a new apple tree notable for its resistance to scab and consistent high productivity, as well as for its flavorful fruit. 'Inolov' is distinguished from its female parent by its scab resistance and late harvest maturity (six weeks after 'X4712' Gala), and from its male parent 'X6908' by the more extensive red overcolor of its fruit. 'X6908' has about 25% red overcolor, as compared to 40% to 60% red overcolor on 'Inolov'.

'Inolov' differs from similar variety 'Gala' (U.S. Plant Pat. No. 3,637) by its later maturity and resistance to common strains of apple scab (*Venturia inaequalis*).

BRIEF DESCRIPTION OF THE PHOTOGRAPHS

Figure 1:
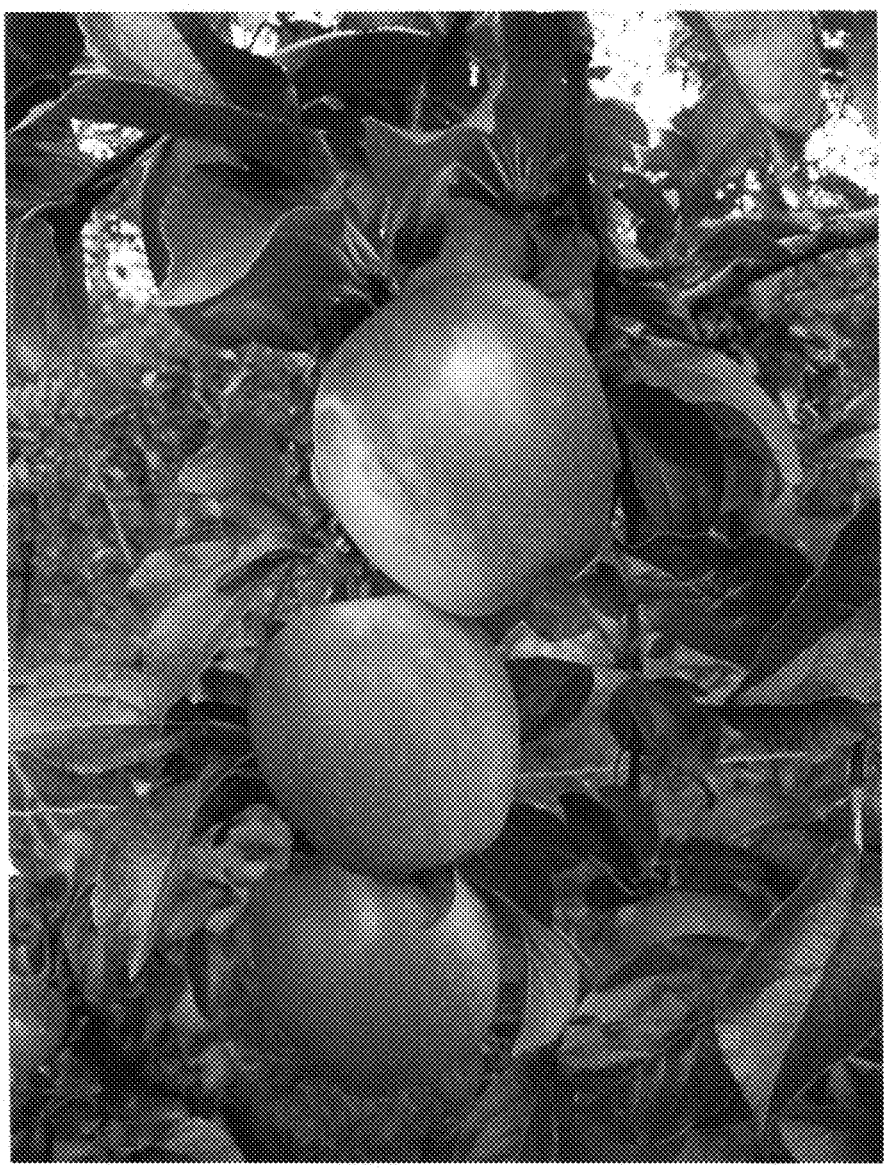
Figure 2:
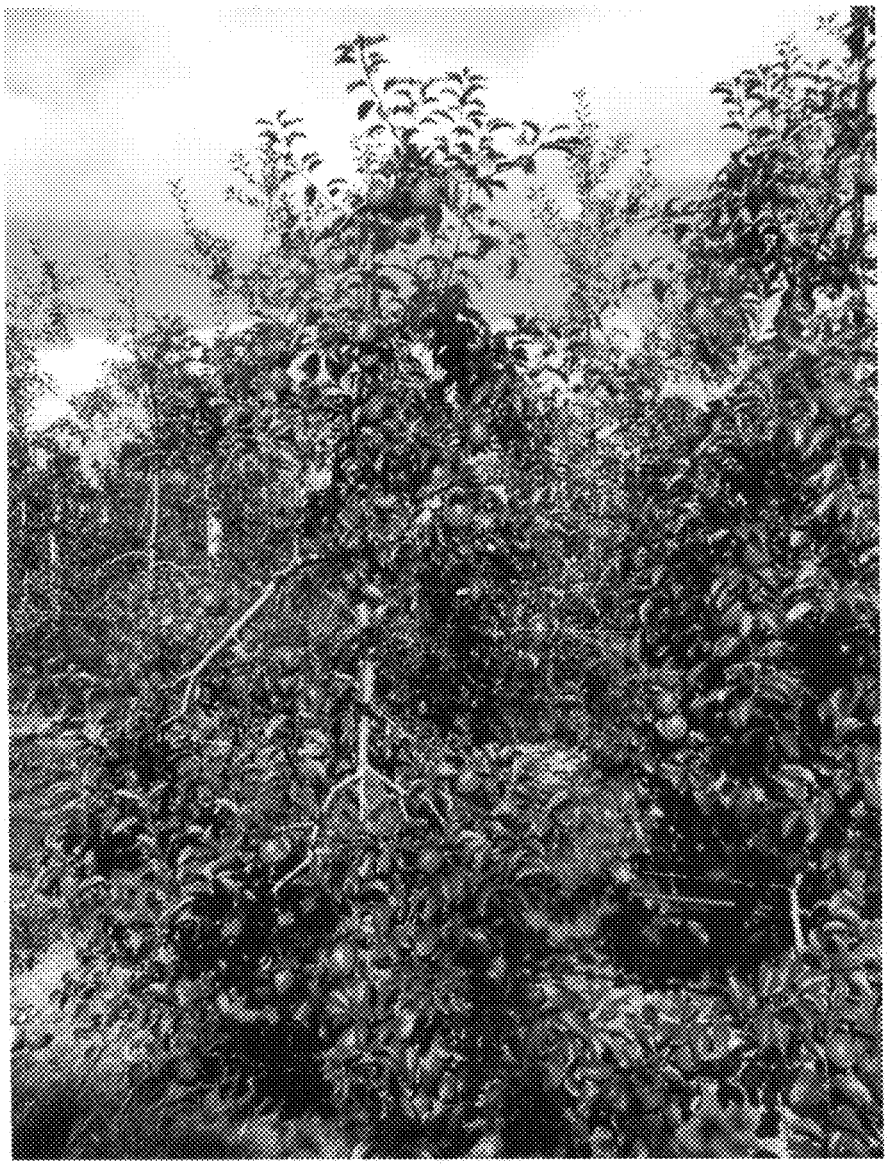
Figure 3:
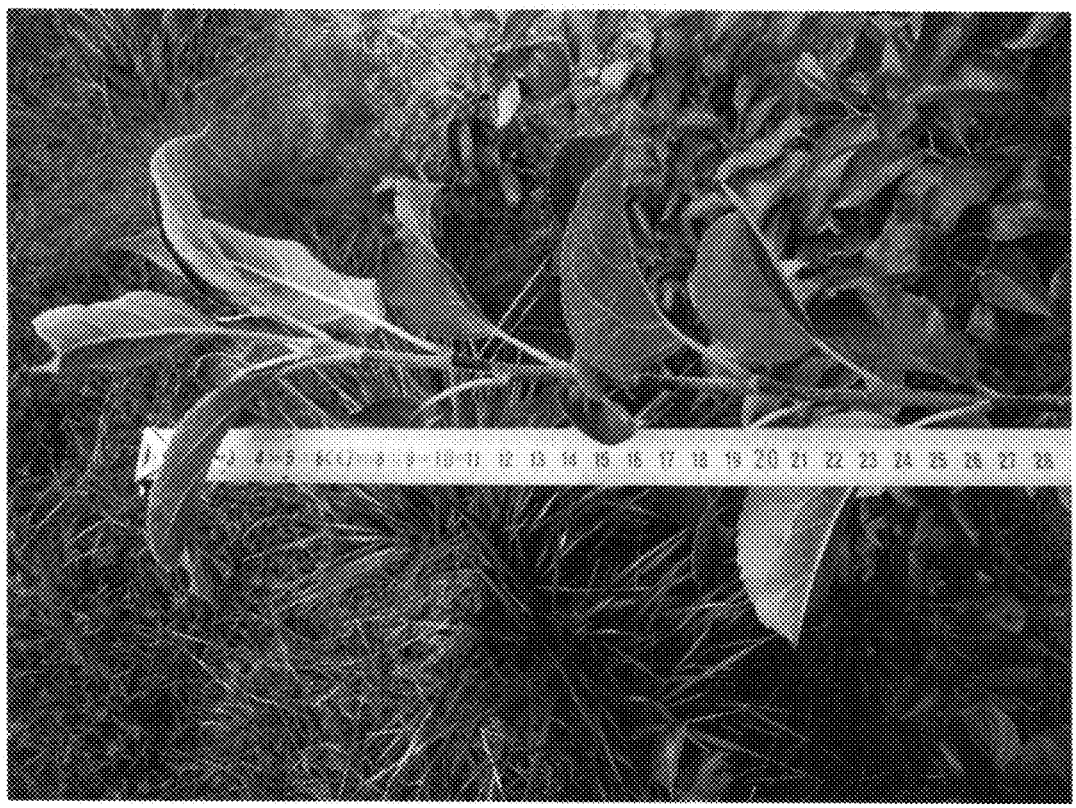
Figure 4:
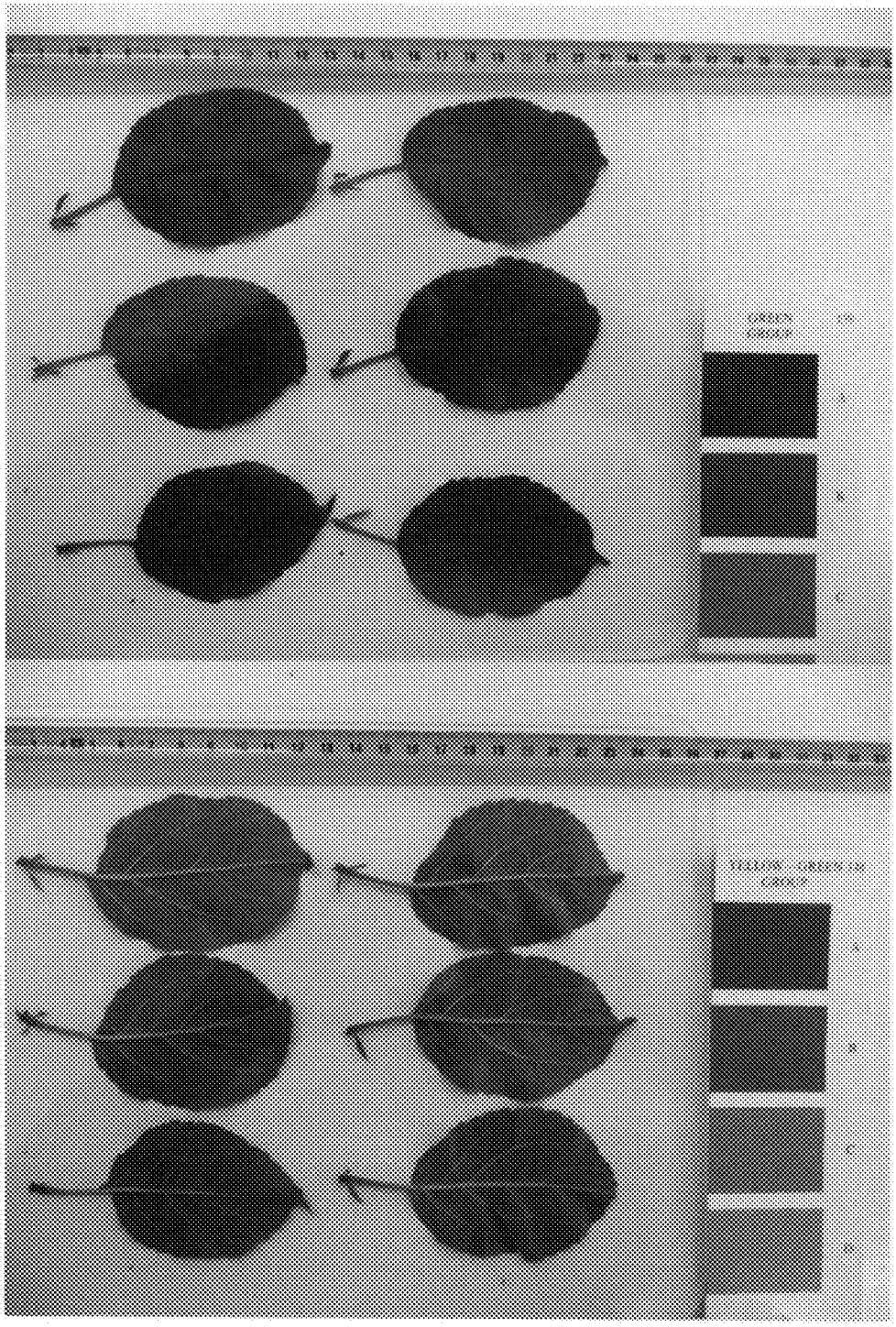
Figure 5:
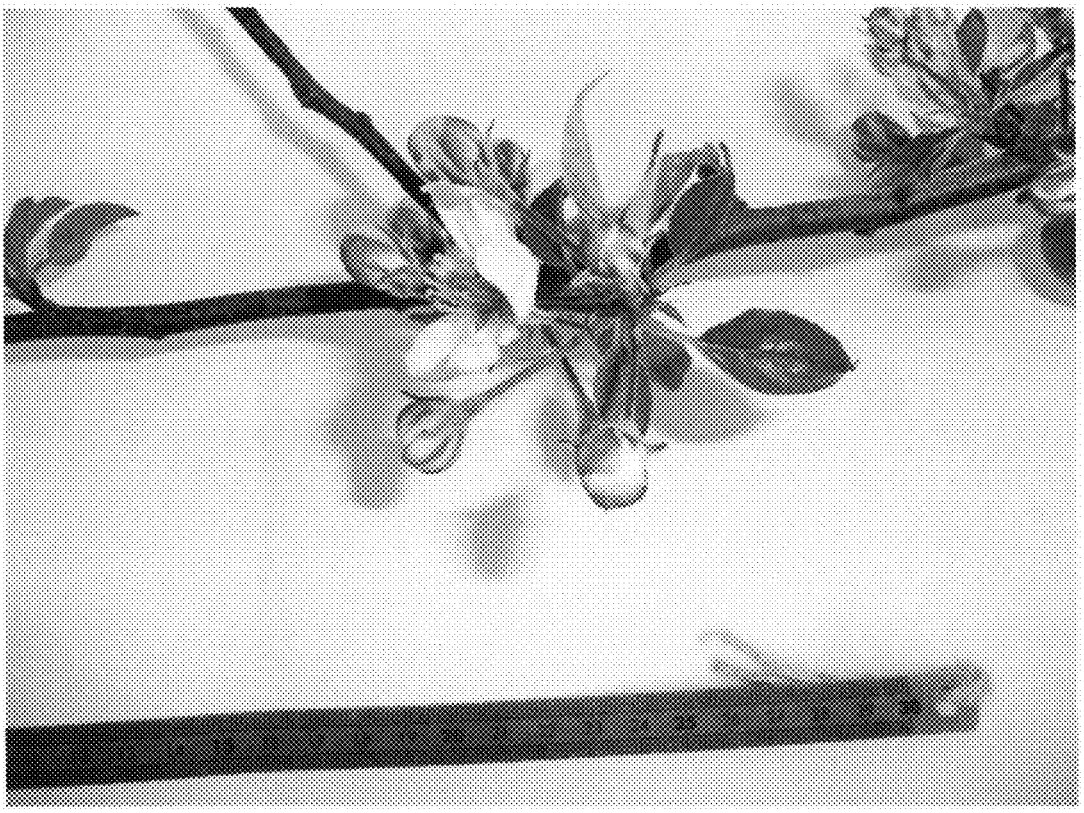
Figure 6:
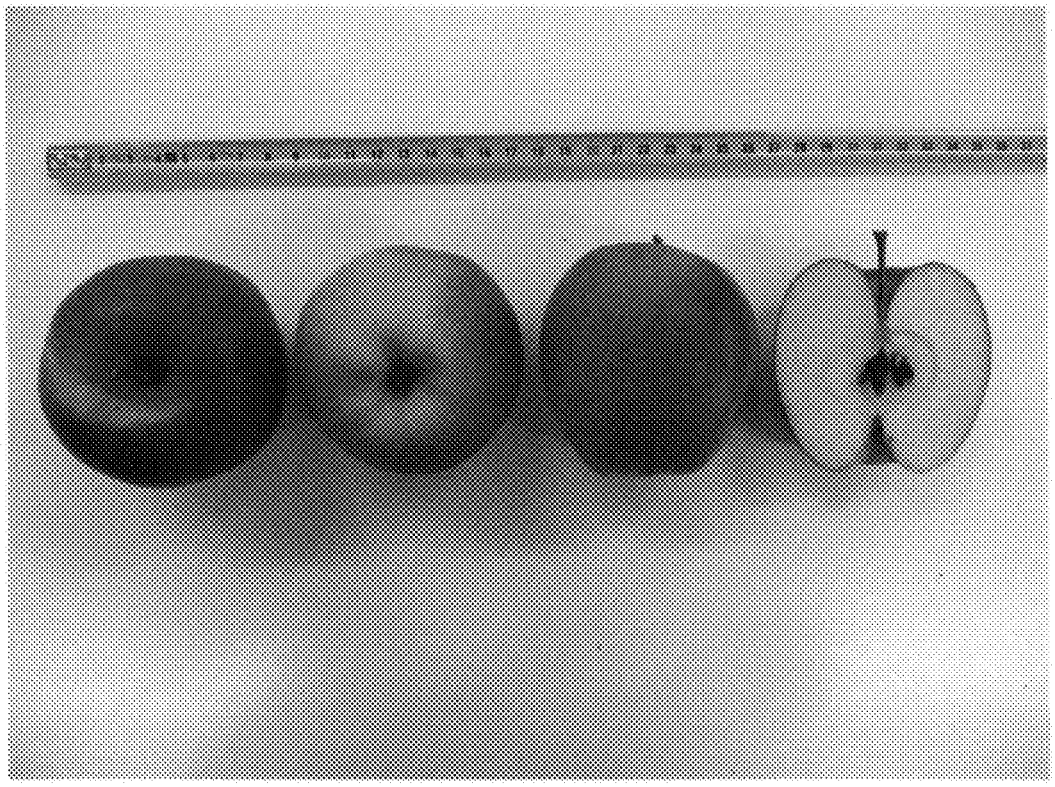

FIG. 1 shows fruit of the new variety on the tree;
FIG. 2 shows a tree of the new variety;

FIG. 3 shows a branch and leaves of the new variety;
FIG. 4 shows upper and lower surfaces of leaves of the new variety;
FIG. 5 shows buds and blossoms of the new variety; and
FIG. 6 shows whole and sectioned fruit of the new variety after harvest.

DETAILED BOTANICAL DESCRIPTION OF THE VARIETY

The following detailed botanical description is based on observations made in 2014 of trees of 'Inolov' in their seventh leaf. The trees were grown at Querré, France on Pajam®2 Cepiland rootstock. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Medium.
*Type*.—Ramified.
*Habit*.—Spreading.
*Height*.—3.70 m.
*Diameter*.—1.5 m.
*Trunk diameter* (*at* 30 *cm above the graft union*).—6.7 cm.
*Bark texture*.—Relatively smoth.
*Bark color*.—Grey-brown 199A.

*Lenticels*.—Length up to 10 mm, height about 0.8 mm; Brown N200D; density about 20 per 10 $cm^2$.

Branch (fruiting branches located at around 1 m above the graft union):

*Length*.—1.30 m.
*Diameter*.—3.5 cm.
*Crotch angle*.—90°.
*Color*.—Greyed-orange 165A.
*Lenticels*.—Length up to 6 mm, height about 0.7 mm; density 3 to 6 per $cm^2$.

1 Year old shoot:

*Length*.—30 cm.
*Coloration*.—Greyed-orange 166A.
*Pubescence*.—Weak to average.
*Thickness*.—4.2 mm.
*Internode length*.—Medium.
*Lenticels*.—Length 0.8 mm to 1.0 mm, height 0.5 mm; yellow-white 158A; density 6 to 8 per $cm^2$.

Winter hardiness:

*Hardiness*.—Temperate.

Flower buds:

*Shape*.—Round.
*Length*.—15 mm.
*Diameter*.—15 mm.
*Coloration*.—Red-purple 67A.

Flowers:

*Colour* (*balloon stage*).—White to red-purple 67A.
*Diameter of open flower*.—40 mm.
*Relative position of petal margin*.—Free to touching.
*Depth*.—10 mm.
*Number per cluster*.—5 to 8.

Petals:

*Number per flower*.—5.
*Shape*.—Ovate.
*Length*.—21 mm.
*Width*.—11 mm.
*Apex*.—Rounded.
*Base*.—Aequilateral.
*Margin*.—Smooth.
*Color of upper surface*.—White N155B with red-purple 70A along center vein and on tips.
*Color of lower surface*.—White N155B.

Pistils:

*Length*.—4 to 5 mm.
*Color*.—Yellow-green 145B.
*Quantity per flower*.—5.

Stigma:

*Length*.—0.8 mm.
*Color*.—Yellow-green 145A.

Style:

*Length*.—7 mm to 8 mm.
*Color*.—Yellow-green 145C.

Ovary:

*Length*.—5.2 mm.
*Color*.—Pubescense obscures color.

Stamen:

*Quantity*.—15 (average).
*Length*.—9.1 mm.
*Is pollen produced*?.—Yes.
*Pollen color*.—Yellow 2C.

Bloom:

*Date of first bloom*.—Apr. 6, 2014.
*Date of full bloom*.—Apr. 8, 2014.

Pedicel:

*Length*.—25 to 33 mm.
*Diameter*.—2 mm.
*Color*.—Green 138B.

Sepals:

*Quantity*.—5.
*Color*.—Lower surface green 139C; upper surface green 139A.
*Length*.—7 mm.
*Width*.—2 mm.
*Shape*.—Pointed.
*Margin*.—Smooth.

Leaves:

*Shape*.—Oval.
*Length*.—8.5 cm.
*Width*.—5.3 cm.
*Blade margin*.—Serrate.
*Apex*.—Acuminate.
*Base shape*.—Rounded.
*Venation*.—Pinnate.
*Vein color*.—Yellow-green 148D.
*Texture*.—Upper surface glossy; lower surface veined.
*Color of top surface*.—Green 139A.
*Color of bottom surface*.—Green 148C.
*Attitude in relation to shoot*.—Upwards to outwards.

Petiole:

*Length*.—25 mm.
*Diameter*.—1.8 mm.
*Color*.—Yellow-green 145C with anthocyanin coloration red-purple 58A at base.
*Stipules*.—1 or 2 per petiole; length 5 mm to 10 mm; width 1 mm to 2 mm; upper surface yellow-green 148B; lower surface yellow green 148B.

Fruit:

*Quantity per cluster*.—1 to 2.
*Apical diameter*.—75 to 80 mm.
*Axial diameter*.—75 to 80 mm.
*Weight*.—200 g.
*General shape in profile*.—Ovoid to cylindrical.
*Position of maximum diameter*.—Toward stem end of the fruit.
*Ribbing*.—Weak.
*Crowning at calyx end*.—Weak to average.
*Aperture of eye*.—Closed.
*Size of eye*.—8 mm.
*Length of sepal*.—3 mm.
*Depth of eye basin*.—18 mm.
*Width of eye basin*.—18 mm.
*Length of stalk*.—33 mm.
*Thickness of stalk*.—2 mm.
*Width of stalk cavity*.—25 mm.
*Depth of stalk cavity*.—23 mm.
*Lenticels*.—Round; diameter 0.3 mm; color yellow 8B; density 3 per $cm^3$.
*Bloom of skin*.—Light.
*Greasiness of skin*.—Weak.
*Background color of skin*.—Yellow 8B.
*Over color of skin*.—Red 53B.
*Amount of over color*.—40% to 60%.
*Intensity of over color*.—Bright.
*Pattern of over color*.—Solid flush with weakly defined stripes.
*Flesh texture*.—Fine.
*Juiciness*.—Juicy.

*Aroma*.—Sweet.

*Brix*.—12° to 13°.

*Flesh color*.—Yellow 11C.

*Locules*.—5 per fruit; length 10 mm; width 6 mm.

*Stem color*.—Greyed-orange 165B.

*Eating quality*.—Firm, crisp, very good taste.

Seeds:

*Quantity per fruit*.—7 to 9.

*Shape*.—Long shape, narrow and pointed.

*Size*.—Length 8 mm; width 4.5 mm.

*Color*.—Brown 200B.

Harvest:

*Amount of fruit produced per harvest*.—20 to 25 kg per tree.

*Harvest date range*.—September 25 to Oct. 2, 2014.

Diseases/pests:

*Resistance*.—Common species of scab (VF).

*Susceptibility*.—None noted.

Storageability: Stores well, 5 months in cold storage (3° C.).

Market use: Fresh market.

I claim:

1. A new and distinct apple tree as described and illustrated herein.

* * * * *